(12) United States Patent
Goda

(10) Patent No.: US 6,378,134 B1
(45) Date of Patent: Apr. 30, 2002

(54) ELASTICALLY STRETCHABLE COMPOSITE SHEET AND DISPOSABLE WEARING ARTICLE USING THIS COMPOSITE SHEET

(75) Inventor: Hiroki Goda, Kagawa-ken (JP)

(73) Assignee: UNI-CHARM Corporation, Ehime-ken (JP)

( * ) Notice: Subject to any disclaimer, the term of this patent is extended or adjusted under 35 U.S.C. 154(b) by 0 days.

(21) Appl. No.: 09/942,721

(22) Filed: Aug. 31, 2001

(30) Foreign Application Priority Data

Sep. 1, 2000 (JP) ........................................ 2000-266195

(51) Int. Cl.[7] .............................. A41B 9/00; A61F 13/20
(52) U.S. Cl. ............... 2/78.3; 2/77; 2/101; 604/385.25; 428/78
(58) Field of Search ............................ 428/77, 78, 101; 604/385.01, 385.25, 385.26, 395.27; 2/76, 78.3, 237

(56) References Cited

U.S. PATENT DOCUMENTS

| 4,606,964 A | * | 8/1986 | Wideman | ................... 428/152 |
|---|---|---|---|---|
| 4,642,819 A | * | 2/1987 | Ales et al. | ...................... 2/400 |
| 4,808,252 A | * | 2/1989 | Lash | .......................... 156/73.1 |
| 6,313,372 B1 | * | 11/2001 | Suzuki | ........................ 604/365 |
| 6,322,547 B1 | * | 11/2001 | Hansson | ................ 604/385.25 |

FOREIGN PATENT DOCUMENTS

JP     62-28456     2/1987

\* cited by examiner

Primary Examiner—John J. Calvert
Assistant Examiner—Robert H. Muromoto, Jr.
(74) Attorney, Agent, or Firm—Lowe Hauptman Gilman & Berner, LLP

(57) ABSTRACT

An elastically stretchable sheet used, for example, as stock material for front and rear waist regions includes an elastically stretchable first sheet, a third sheet longer than said first sheet and bonded to said first sheet so as to form pleats, and a second sheet longer than said first and third sheets and bonded directly or indirectly to said first sheet so as to form pleats.

4 Claims, 6 Drawing Sheets

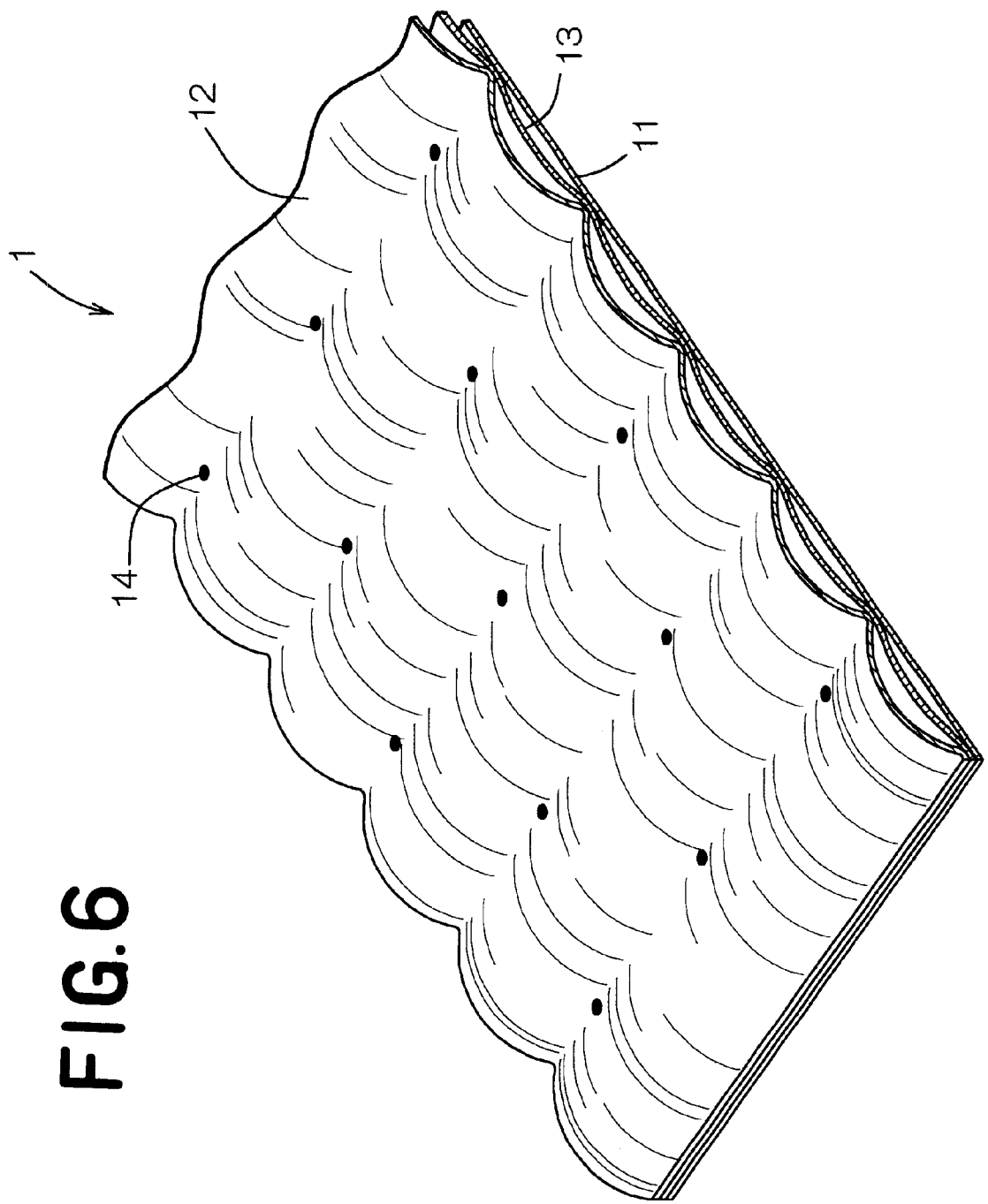

ELASTICALLY STRETCHABLE COMPOSITE SHEET AND DISPOSABLE WEARING ARTICLE USING THIS COMPOSITE SHEET

BACKGROUND OF THE INVENTION

This invention relates to an elastically stretchable composite sheet and a disposable wearing article using this composite sheet.

The elastically stretchable composite sheet comprising an elastically stretchable sheet and an inelastically stretchable sheet bonded together intermittently in a direction in which these sheets are stretchable is well known, for example, from Japanese Patent Application Publication No. 1987-28456A. In this composite sheet of well known art, the inelastically stretchable sheet is formed with a plurality of pleats arranged in the direction in which this sheet is stretchable.

In one practical use of such an elastically stretchable material for the wearing article, it is intended to increase a stretching stress of this material sharply as soon as it has been stretched to a certain limit of stretching. For example, the elastic member associated with a waist-opening of a pants-type disposable diaper or training pants is adjusted so that while this elastic member does not positively lace the wearer's waist so far as no brisk movement of the wearer occurs, wearer's waist is positively laced by the elastic member and the diaper or the pants are prevented from slipping down because the lacing effect of the elastic member sharply increases as the brisk movement of the wearer's body further stretches the elastic member. It should be understood here that the lacing effect of the elastic member varies progressively, e.g., in two or three steps, rather than abruptly varies.

In the case of the composite sheet well known from the Japanese Patent Application Publication No. 1987-28456A, the elastically stretchable sheet is elastically stretched and at the same time the pleats of the inelastically stretchable sheet come out as the composite sheet is stretched. After the composite sheet has been stretched until the pleats completely come out, a stretching stress of the composite sheet abruptly increases since the elastically stretchable sheet must be stretched together with the inelastically stretchable sheet. While such composite sheet of well known art is certainly one of the elastically stretchable materials suitable for use in the pants-type disposable diaper, it is a problem accompanying this composite sheet that the stretching stress abruptly varies at once.

SUMMARY OF THE INVENTION

In view of the problem as has been described above, it is an object of this invention to provide the elastically composite sheet improved so that its stretching stress may be varied at least in two steps. A second object of this invention is to provide a pants-type disposable wearing article using such composite sheet to achieve an improvement such that the wearing article may be easily put on a wearer's body and prevented from slipping down once the article has been put on the wearer's body.

According to one aspect of this invention, there is provided an elastically stretchable composite sheet comprising a first sheet having x- and y-directions orthogonal to each other and being elastically stretchable at least in the y-direction and a second sheet being inelastically stretchable at least in the y-direction wherein the first and second sheets are bonded intermittently in the y-direction to form the composite sheet adapted to be elastically stretchable in the y-direction.

The improvement in the elastically stretchable composite sheet according to this invention is in that a third sheet being elastically stretchable in the y-direction and having a dimension in the y-direction longer than the first sheet is bonded to at least one surface of the first sheet intermittently in the y-direction so that the third sheet has a plurality of pleats formed due to a dimension by which the third sheet is longer than the first sheet in the y-direction, and the second sheet having a dimension in the y-direction longer than both the first and third sheets is bonded to the first directly or indirectly by means of the third sheet so that the second sheet has a plurality of pleats formed due to a dimension by which the second sheet is longer than the first sheet in the y-direction.

The second object set forth above is achieved, according to the other aspect of this invention, there is provided a pants-type disposable wearing article comprising a front waist region, a rear waist region and a crotch region extending between these two waist regions wherein the two waist regions are bonded together along transversely opposite side edge portions of the respective two waist regions to form a pants-type structure.

The improvement in the pants-type disposable wearing article according to this invention is in that the front and rear waist regions are at least partially formed by a composite sheet having elastic stretchability in a circumferential direction of the wearing article wherein the composite sheet comprises (1) a first sheet having elastic stretchability in the circumferential direction, (2) a third sheet having a dimension in the circumferential direction longer than the first sheet and elastic stretchability in the circumferential direction, the third sheet being bonded to the first sheet intermittently in the circumferential direction so that the third sheet has a plurality of pleats formed due to a dimension by which the third sheet is longer than the first sheet in the circumferential direction and (3) a second sheet having a dimension in the circumferential direction longer than both the first and third sheets and inelastic stretchability in the circumferential direction, the second sheet being bonded to the first directly or indirectly by means of the third sheet so that the second sheet has a plurality of pleats formed due to a dimension by which the second sheet is longer than the first sheet in the circumferential direction.

BRIEF DESCRIPTION OF THE DRAWINGS

FIG. 6 is a view similar to FIG. 1 but showing an alternative embodiment of this invention.

DETAILED DESCRIPTION OF THE PREFERRED EMBODIMENTS

Details of an elastically stretchable composite sheet and a pants-type disposable wearing article using this composite sheet will be more fully understood from the description given hereunder with reference to the accompanying drawings.

Figure 1:
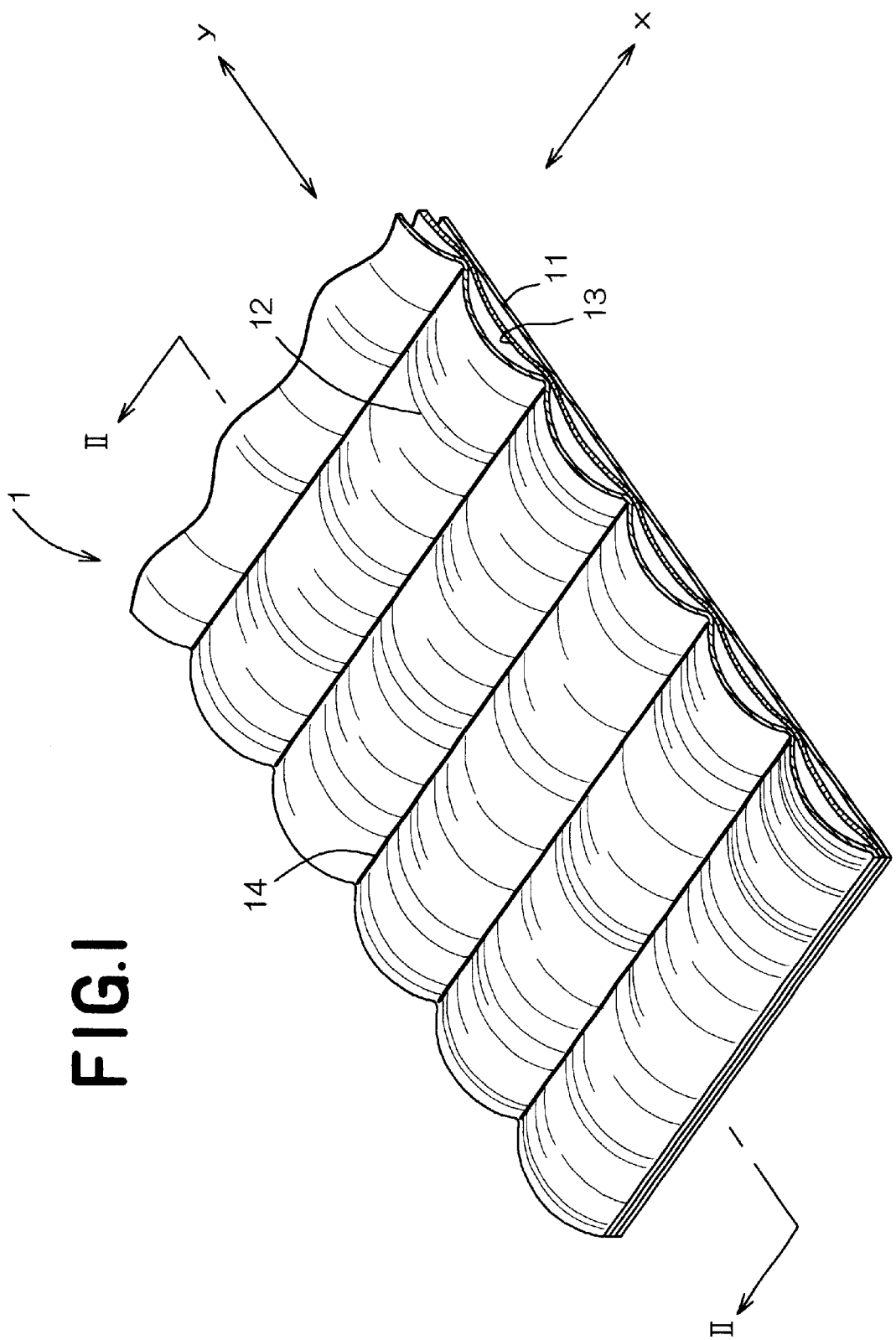
FIG. 1 is a perspective view showing a composite sheet according to this invention.

An elastically stretchable composite sheet 1 shown by FIG. 1 in a perspective view has a x-direction and a y-direction orthogonal to the x-direction and elastically stretchable at least in the y-direction. Such composite sheet 1 comprises a first sheet 11 defining the lowermost layer, a second sheet 12 defining the uppermost layer and a third sheet 13 disposed between these first and second sheets 11, 12 wherein these first ~third sheets 11~13 are welded or adhesively bonded together in a plurality of bonding zones 14. In the illustrated embodiment, the bonding zones 14 are provided in the form of a plurality of bonding lines extending in parallel one to another in the x-direction and arranged intermittently in the y-direction.

Figure 2:
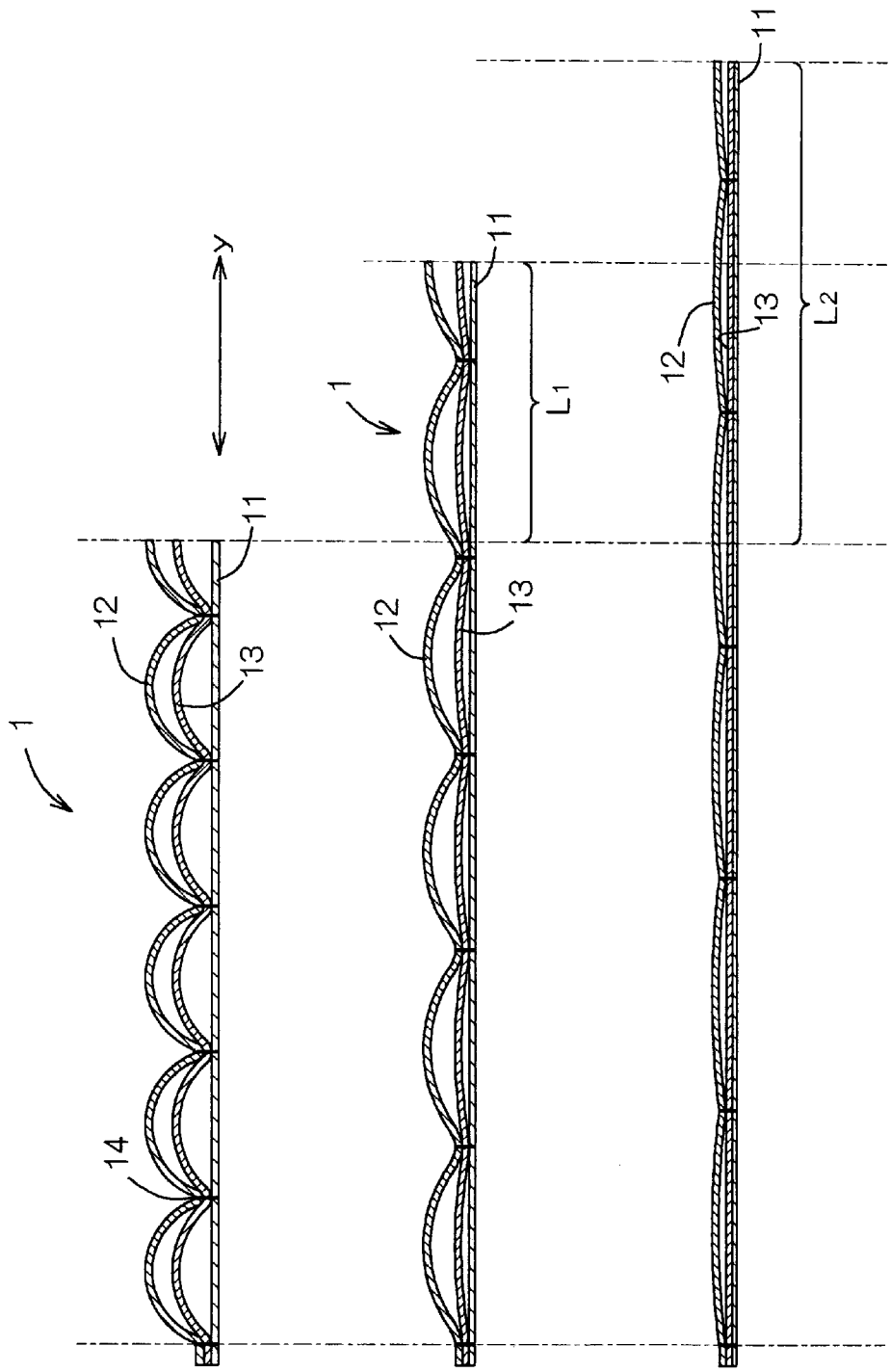
FIG. 2 is sectional views taken along a line II—II in FIG. 1 before the composite sheet is stretched (A) and in successively stretched states (B) and (C)

Of FIG. 2, (A) is a sectional view taken along a line II—II in FIG. 1 and (B) and (C) are sectional views similar to (A) except that the composite sheet 1 has been stretched in the y-direction by $L_1$ and $L_2$ (See FIG. 3), respectively. The first sheet 11 extends in the x- and y-directions so as to maintain a substantially flat state and the second sheet 12 curves upward between each pair of the adjacent bonding zones 14 to describe a circular arc. Such circular arc is repeated in the y-direction and a plurality of pleats undulating in the y-direction are formed by the first sheet 11 as a whole. The third sheet 13 also curves upward between each pair of the adjacent bonding zones 14 to describe a circular arc between the first sheet 11 and the second sheet 12. Similar to the second sheet 12, the third sheet 3 forms as a whole a plurality of pleats undulating in the y-direction. Between each pair of the adjacent bonding zones 14, 14, the circular arc described by the second sheet 12 is longer than the circular arc described by third sheet 13. The first~third sheets 11~13 are bonded together in the bonding zones of the composite sheet 1 common to these three sheets 11~13.

In the composite sheet having such cross-sectional shape, the first sheet 11 is elastically stretchable at least in the y-direction at least by 20%, preferably by 100% or higher and more preferably by 200% or higher. Such first sheet 11 may be formed with a nonwoven for woven fabric of elastically stretchable fiber such as a styrene-based elastomer or urethane-based fiber or elastically stretchable film made of elastomer with a basis weight in a range of 5~200 g/m². The second sheet 12 is inelastically stretchable at least in the y-direction and may be formed, for example, with a nonwoven or woven fabric made of inelastically stretchable fiber such as polyethylene-, polypropylene-, nylon- or polyester-based fiber having a fineness, for example, of 0.1~50 μm with a basis weight in a range of 2~100 g/m². The third sheet 13 also is elastically stretchable at least in the y-direction similarly to the first sheet 11 and may be formed with a nonwoven or woven fabric made of elastically stretchable fiber or elastically stretchable film or the like with a basis weight of 5~200 g/m².

Figure 3:
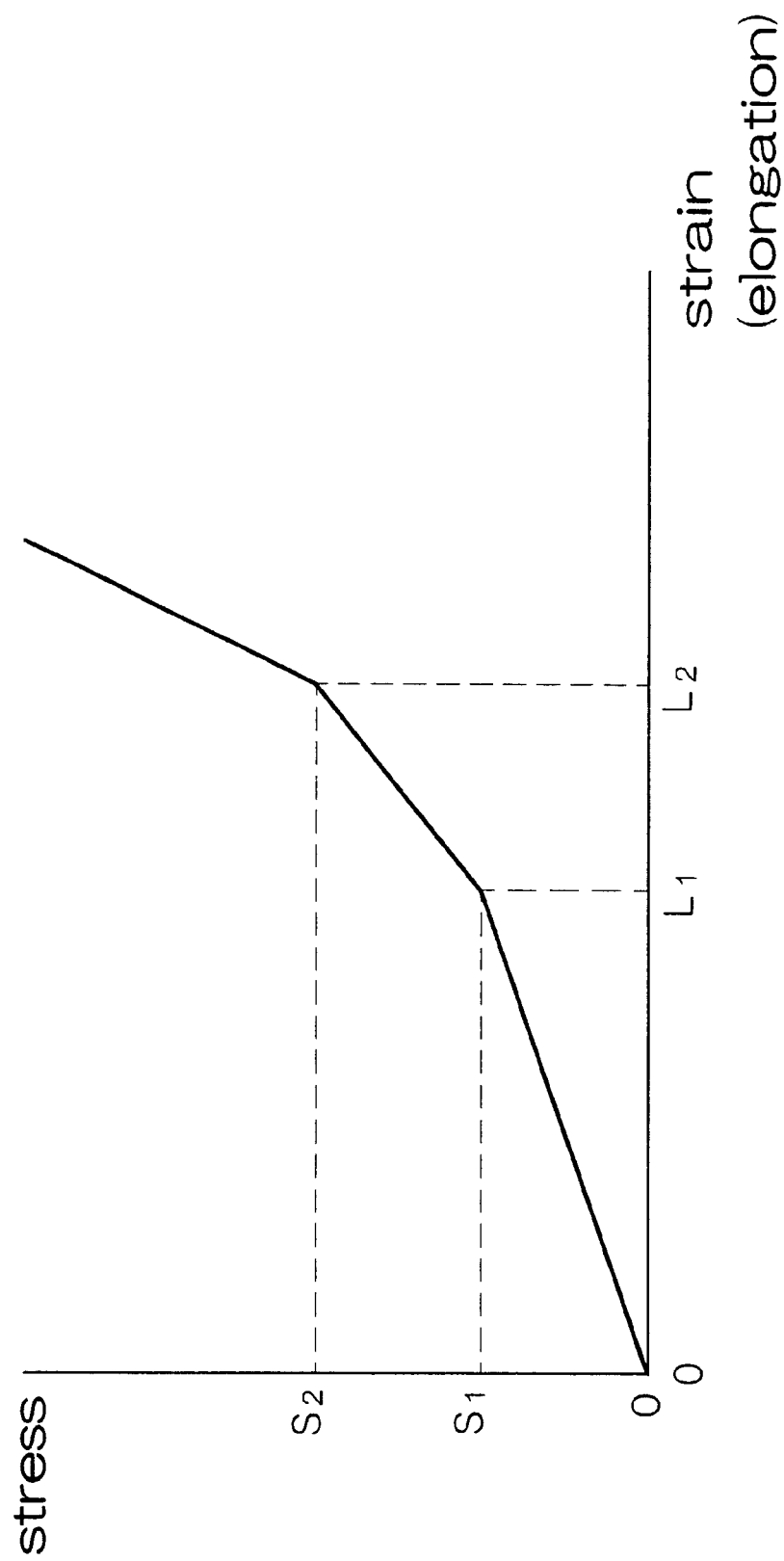
FIG. 3 is a graphic diagram plotting a relationship between stress and strain in stretching the composite sheet.

FIG. 3 is a graphic diagram plotting a relationship between stress and strain (elongation) observed in stretching the composite sheet 1. As will be apparent from FIGS. 2 and 3, the first sheet 11 is elastically stretched as the composite sheet 1 of FIG. 2(A) is stretched by a length $L_1$ and thereupon the stretching stress of the composite sheet 1 reaches a value $S_1$. The pleats of the second and third sheets 12, 13 progressively come out and the height of the circular arcs of these sheets 12, 13 gradually reduced as the composite sheet 1 is stretched by the length $0~L_1$. The pleats of the third sheet 13 completely come out as seen in FIG. 2(B) as the composite sheet 1 has been stretched by the length $L_1$. After the composite sheet 1 has stretched by a length exceeding the length $L_1$, a force required to stretch the composite sheet 1 corresponds to a force required to stretch the first sheet 11 plus a force required to stretch the third sheet 13. In other words, a straight line in FIG. 3 abruptly becomes steep and, at the same time, the circular arcs formed by the second sheet 12 are progressively flattened. The pleats of the second sheet 12 completely come out as seen in FIG. 2(C) after the composite sheet 1 has been stretched by a length $L_2$. After the composite sheet 1 has been stretched by a length exceeding the length $L_2$, in addition to the force required to stretch the first and second sheets 11, 13, a force required for inelastically stretching the second sheet 12. Consequently, the straight line in FIG. 3 becomes further steep. During such process of stretching the composite sheet 1, preferably the first and third sheets 11, 13 are still elastically stretchable even after the pleats of the second sheet 12 have completely come out. Relieved of the stretching force, the composite sheet 1 restores its initial state as shown in FIG. 1 substantially by an elastic recovering force of the first sheet 11.

Figure 4:
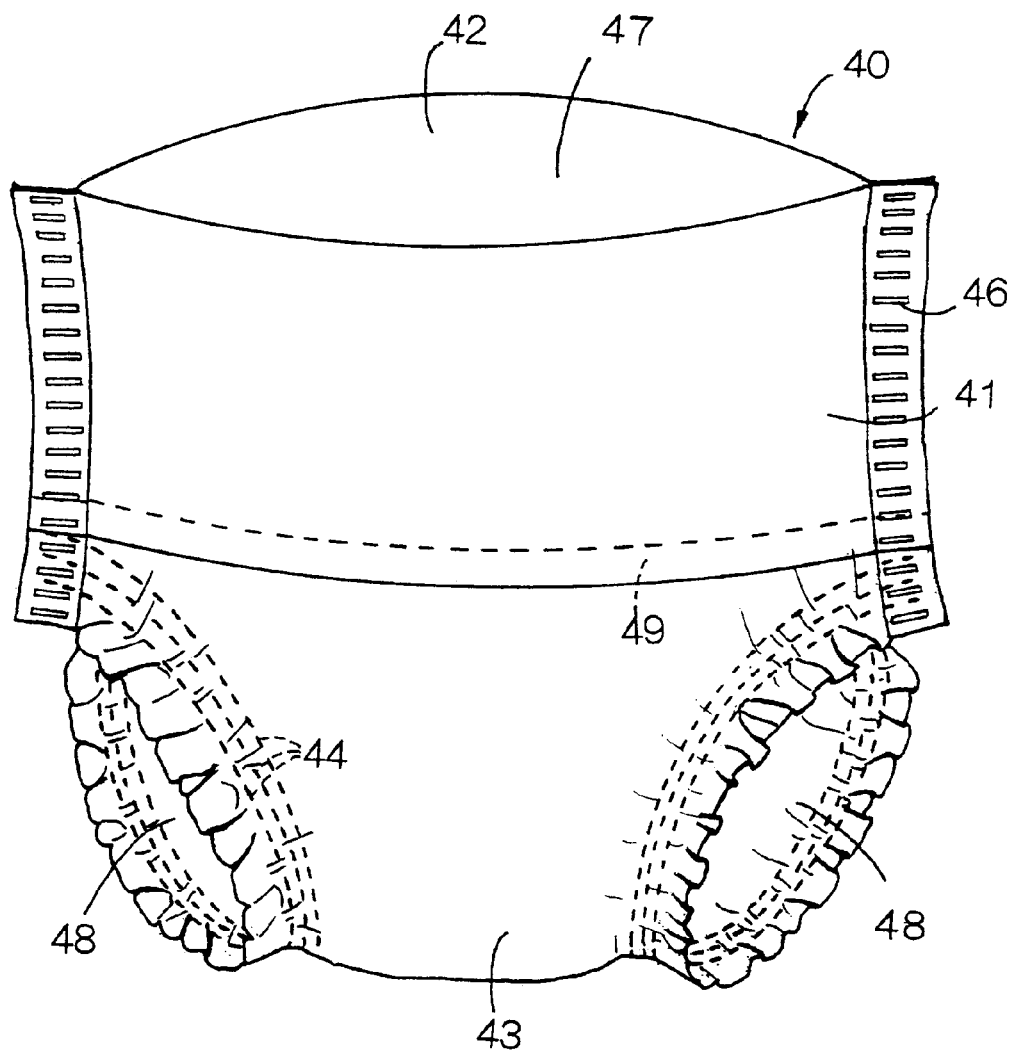
FIG. 4 is a perspective view showing training pants using the composite sheet.

FIG. 4 is a perspective view showing training pants 40 as a typical embodiment of the disposable wearing article using the composite sheet 1 according to this invention. The training pants 40 are composed of a front waist region 41, a rear waist region 42 and a crotch region 43 wherein the front and rear waist regions 41, 42 have respective side edge portions put flat and welded together at welding spots 46 so as to define a waist-opening 47 and a pair of leg-openings 48. The composite sheet 1 is used as stock material for at least one, preferably both of the front and rear waist regions 41, 42 with the y-direction of the composite sheet 1 conformed with a waist-surrounding direction of the training pants 40 so that the composite sheet 1 may be elastically stretchable in the waist-surrounding direction. Water-absorbent nonwoven fabric is used as stock material for the crotch region 43 and overlapped upon and bonded to the composite sheet 1 along bonding zones 49. In the crotch region 43, the nonwoven fabric absorbs urine discharged thereon and gives a crotch region of a wearer of the pants 40 a remarkable feeling wetness to achieve a training effect by wearing such pants 40. Such nonwoven fabric is provided along peripheral edge portions of the respective leg-openings 48 with rubber threads 44 attached under tension thereto.

To use the composite sheet 1 as stock material for the training pants 40, the first~third sheets 11~13 are preferably adjusted so that, referring to FIG. 3, $S_1$=2.5 N/25 mm for $L_1$=105% and $S_2$=10 N/25 mm for $L_2$=115%. The dimension "25 mm" described here should be understood to be a width of the composite sheet 1 as measured in a vertical direction of the training pants 40. The training pants 40 of which the front and rear waist regions 41, 42 are formed by such composite sheet 1 is preferably made so that these front and rear waist regions 41, 42 may be stretched with 35~65% in the waist-surrounding direction after the training pants 40 has been put on the wearer's body and the wearer's mother may stretch the training pants 40 by in the order of 115% at the most in the waist-surrounding direction to put the training pants 40 on the wearer's body. With such training pants 40 put on the wearer's body, the stretching stress of the composite sheet 1 is relatively low and it is not apprehended that the composite sheet 1 might uncomfortably lace the wearer's waist. However, if brisk movement of the wearer's body causes the composite sheet to be stretched at a high ratio, the stretching stress will abruptly increase and reliably prevents the training pants 40 from slipping down. In addition, the wearer's mother intends to widen the waist-opening 47 until the composite sheet 1 is stretched by $L_1$ or $L_2$ in order to put the training pants 40 on the wearer's body, the stretching stress of the composite sheet 1 abruptly increases and makes the mother feel it difficult to widen the waist-opening 47 further. With a consequence, there is no anxiety that the wearer's mother might excessively widen the opening 47 until the front and rear waist regions 41, 42 might be peeled off from each other at the welding spots 46 or the composite sheet 1 forming the front and rear waist regions 41, 42 might be broken.

With the training pants 40 of such arrangement, a welding strength for the front and rear waist regions 41, 42 at the welding spots 46 can be adjusted to be relatively low, for example, in the order of 12 N/25 mm so that the front and rear waist regions 41, 42 may be easily peeled off from each other along the respective side edge portions thereof when it is desired to take off the training pants 40. While the entire areas of the front and rear waist regions 41, 42 may be formed with the composite sheet 1 to make these entire areas stretchable, it is also possible to use the composite sheet 1 as stock material only for portions of the front and rear waist regions 41, 42 so that these front and rear waist regions may be partially stretchable. It should be understood that the illustrated embodiment of the training pants 40 does not intend to limit use of the composite sheet 1 for the front and rear waist regions 41, 42. Specifically, it is possible to use the composite sheet 1 not only for the front and rear waist regions 41, 42, but also for the crotch region 43 or to use the composite sheet 1 only for the crotch region 43.

Figure 5:
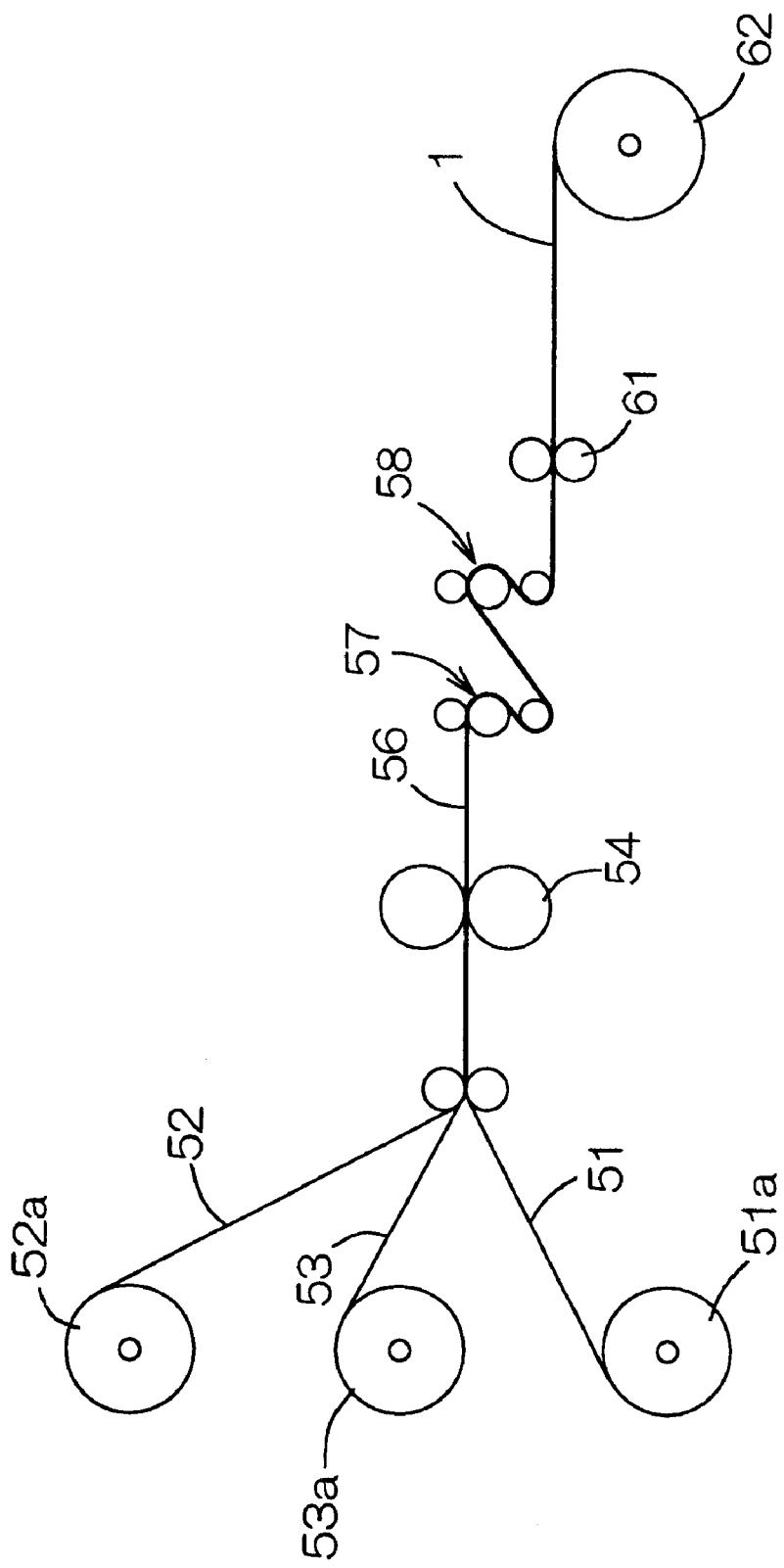
FIG. 5 is a schematic diagram illustrating a process for making the composite sheet.

FIG. 5 is a schematic diagram illustrating an example of a process for making the composite sheet 1. A first web 51 of elastically stretchable nonwoven or woven fabric or film is fed from a first roll 51a provided at the left side in FIG. 5. This first web 51 is formed, for example, with 15 μm diametered continuous fibers of styrene-based elastomer with a basis weight of 10 g/m² and an elastic stretchability of 150% or higher. A second web 52 of inelastically stretchable nonwoven or woven fabric or film is fed from a second roll 52a. The second web 52 is formed, for example, with 15 μm diametered continuous fibers of polypropylene with a basis weight of 15 g/m² and an inelastic stretchability of 150% or higher. A third web 53 of nonwoven or woven fabric or film is fed from a third roll 53a. The third web 53 is elastically stretchable but has a significant permanent set remaining after contraction. The third web 53 is fed in the form of nonwoven fabric formed, for example, by 15 μm diametered continuous fibers obtained by blending styrene-based elastomer and polypropylene, of which 60% elastically contracts and 90% remains as the permanent set after this web 53 has been stretched by 150%.

In the illustrated embodiment of the process, these first~third layers of web 51~53 are guided together into a nip defined between a pair of heated embossing rolls 54 in which these layers of web 51~53 are bonded together in the bonding zones 14 (See FIG. 1) arranged intermittently in the machine direction to form composite web 56. In the course defined between a set of first stretching rolls 57 and a set of second stretching rolls 58, the composite web 56 is stretched at a desired ratio, for example, at a ratio of 150%. To achieve this stretching ratio, these first and second stretching rolls 57, 58 are arranged so that a peripheral speed of the second stretching rolls 58 is higher than that of the first stretching rolls 57. The composite web 56 having been stretched in this manner is relieved of such stretching effect before the composite web 56 reaches a pair of lead-on rolls 61 and leaves these lead-on rolls 61 in the form of continuous composite sheet 1 which is then batched in the form of a roll 62.

In the course of such process, the first web 51 as the component of the composite web 56 is elastically stretched by 150% and then elastically contracts approximately by 150% as the composite web 56 is stretched, for example, by 150% and then relieved of such stretching effect. The second web 52, on the other hand, is elastically stretched by 150% and its substantially whole length having been stretched in this manner is permanently set as the first web 51 contracts. As a result, the length of the second web 52 having been stretched contracts and forms a plurality of pleats as the first web 51 contracts. Of the third web 53 having been stretched by 150%, 60% can elastically contract but 90% is permanently set, so the length permanently set in this manner contracts to form a plurality of pleats as the first web 51 contracts. The pleats formed by these second and third layers of web 52, 53 prevent the first web 51 from completely restoring it initial dimension.

While the second and third layers of web 52, 53 are fed onto the upper surface of the first web 51 in the illustrated embodiment of the process, it is also possible to obtain the composite web 56 by feeding the second web 52 and/or the third web 53 also onto the lower surface of the first web 51.

FIG. 6 is a view similar to FIG. 1 but illustrating an alternative embodiment of this invention. The composite sheet 1 according to this embodiment comprises the first~third sheets 11~13 welded together at welding spots 14 arranged intermittently not only in the x-direction but also in the y-direction. In such composite sheet 1, the welding spots 14 are appropriately scattered over the sheet 1 and therefore it is not apprehended that these welding spots 14 might give the wearer uncomfortable feeling when the composite sheet 1 comes in contact with the wearer's skin.

The composite sheet according to this invention enables the force required to stretch the composite sheet in the y-direction to be varied in two steps since the composite sheet the elastically stretchable sheet and the inelastically stretchable sheet are bonded to the basic elastically stretchable sheet so that the first-mentioned elastically stretchable sheet and the inelastically stretchable sheet may form a plurality of pleats arranged in the x- and y-directions, at least in they-direction. The disposable pants-type wearing article using such composite sheet as stock material for the front and rear waist regions can avoid the inconvenience that the wearing article might uncomfortably lace the wearer's waist. In addition, even when the wearer's mother widen the waist-opening to put the article on the wearer's body, there is no anxiety that the composite sheets bonded together along the respective side edge portions of these sheets might be broken or peeled off.

What is claimed is:

1. An elastically stretchable composite sheet comprising a first sheet having x- and y-directions orthogonal to each other and being elastically stretchable at least in said y-direction and a second sheet being inelastically stretchable at least in said y-direction wherein said first and second sheets are bonded intermittently in said y-direction to form the composite sheet adapted to be elastically stretchable in said y-direction, wherein:

a third sheet being elastically stretchable in said y-direction and having a dimension in said y-direction longer than said first sheet is bonded to at least one surface of said first sheet intermittently in said y-direction so that said third sheet has a plurality of pleats formed due to a dimension by which said third sheet is longer than said first sheet in said y-direction; and said second sheet having a dimension in said y-direction longer than both said first and third sheets is bonded to said first directly or indirectly by means of said third sheet so that said second sheet has a plurality of pleats formed due to a dimension by which said second sheet is longer than said first sheet in said y-direction.

2. The composite sheet according to claim 1, wherein elastically stretchable extents of said first and third sheets in said y-direction exceed a length of said composite sheet having been stretched in said y-direction until the pleats of said second sheet disappear.

3. The composite sheet according to claim 1, wherein said first~third sheets are bonded together in bonding zones of said composite sheet common to these three sheets.

4. A pants-type disposable wearing article comprising a front waist region, a rear waist region and a crotch region extending between these two waist regions wherein said two waist regions are bonded together along transversely opposite side edge portions of the respective two waist regions to form a pants-type structure, said pants-type disposable wearing article further comprising said front and rear waist regions being at least partially formed with a composite sheet having elastic st retchability in a circumferential direction of said wearing article wherein said composite sheet comprises (1) a first sheet having elastic stretchability in said circumferential direction, (2) a third sheet having a dimension in said circumferential direction longer than said first sheet and elastic stretchability in said circumferential direction, said third sheet being bonded to said first sheet intermittently in said circumferential direction so that said third sheet has a plurality of pleats formed due to a dimension by which said third sheet is longer than said first sheet in said circumferential direction and (3) a second sheet having a dimension in said circumferential direction longer than both said first and third sheets and inelastic stretchability in said circumferential direction, said second sheet being bonded to said first directly or indirectly by means of said third sheet so that said second sheet has a plurality of pleats formed due to a dimension by which said second sheet is longer than said first sheet in said circumferential direction.

* * * * *